United States Patent [19]
Godai et al.

[11] 4,192,175
[45] Mar. 11, 1980

[54] PROCESS AND APPARATUS FOR MEASUREMENT OF DIFFUSIBLE HYDROGEN

[75] Inventors: Tomokazu Godai; Tohru Sugiyama, both of Kamakura; Morihiko Sugino; Masaru Kondo, both of Fujisawa; Tsuneshi Ogawa, Kamakura, all of Japan

[73] Assignee: Kobe Steel, Ltd., Kobe, Japan

[21] Appl. No.: 883,235

[22] Filed: Mar. 3, 1978

[51] Int. Cl.$^2$ .............................................. G01N 7/14
[52] U.S. Cl. ......................................................... 73/19
[58] Field of Search ............................ 73/19, 23, 23.1

[56] References Cited

U.S. PATENT DOCUMENTS

| | | | |
|---|---|---|---|
| 2,991,684 | 7/1961 | Wever et al. | 73/19 |
| 3,176,500 | 4/1965 | Coe | 73/19 |
| 3,251,217 | 5/1966 | Evens et al. | 73/19 |
| 3,427,863 | 2/1969 | Schultz | 73/19 |
| 3,498,105 | 3/1970 | Hetherington | 73/19 |
| 3,949,590 | 4/1976 | Boillot | 73/19 |

FOREIGN PATENT DOCUMENTS 2727252  12/1977  Fed. Rep. of Germany .............. 73/19

OTHER PUBLICATIONS

Feichtinger et al., "A Contribution to Behavior and Determination of Hydrogen During and After Welding", and WRI File, *Welding Research International*, vol. 6, No. 3, pp. 1–10, 1976.

Hargrove et al., "Determination of Nitrogen and Hydrogen at Parts-Per-Million Levels in Steel", *Analytical Chemistry*, vol. 43, No. 3, pp. 439–442, Mar. 1971.

*Primary Examiner*—Stephen A. Kreitman
*Attorney, Agent, or Firm*—Oblon, Fisher, Spivak, McClelland & Maier

[57] ABSTRACT

The invention is a process and apparatus for measurement of diffusible hydrogen within a metal, in which a metal sample is placed within an enclosed collector vessel for a predetermined time and at a predetermined temperature, and the total resultant effused gases within the collector vessel are fed to a gas chromatograph.

4 Claims, 11 Drawing Figures

PROCESS AND APPARATUS FOR MEASUREMENT OF DIFFUSIBLE HYDROGEN

BACKGROUND OF THE INVENTION

1. Field of the Invention

This invention relates to a process and an apparatus for measurement of small amounts of diffusible hydrogen within steels or weld metals.

2. Description of Prior Art

A small amount of hydrogen exists in steels or weld metals, and it is classified as residual hydrogen or diffusible hydrogen depending upon its behavior. It is known that the solubility of hydrogen in steel near its melting point is approximately 25 ppm at 1800° C. under $P_{H_2}=1$ atm. If such hot steel is quenched, the solubility of hydrogen suddenly drops and hydrogen gradually moves out of the steel crystal lattice. However, as the temperature of the steel drops, the hydrogen effusion rate is reduced, and the rate is $10^{-4}14\ 10^{-6}$ cm$^2$/sec. at room temperature. If a portion of the diffusible hydrogen gathers at some part of the steel lattice, this may cause cold cracking. Now, cold cracking of a weld joint can be considered as follows. Hydrogen which has effused from a deposited metal during cooling before completion of solidification immediately after welding does not affect the occurrence of cracks, while hydrogen which effuses after solidification does adversely affect the occurrence of cracks. In order to determine whether there is a strong relationship between retained diffusible hydrogen in the weld metal after quenching and the occurrence of cracks, hydrogen content has been measured with respect to welding material of high hydrogen level, thus the above mentioned consideration is correct with inaccurate measurement of diffusible hydrogen. Based on these results, the total amount of diffusible hydrogen can be accurately measured by measuring a predetermined ratio of diffusible hydrogen using a constant time period from completion of welding to start of coolng and a constant cooling rate. Accordingly, the presently available standardized methods, the JIS method and the IIW method, strictly restrict cooling conditions.

The above noted JIS method is JIS Z 3113-1975, in which a sample piece which has been cooled under restricted conditions is immersed in glycerine and effused gas displaces glycerine in a burette then the burette; scale is read. While, in accordance with the IIW method, mercury is used as collector liquid instead of glycerine as in the JIS method. However these methods have the following problems, respectively.

(1) glycerine is apt to absorb hydrogen, so that hydrogen recovery is 50–75% compared wth that of the IIW method.

(2) glycerine is highly viscous and the effused gas rising velocity in glycerine is approximately 0.01% of that in mercury. So it is difficult to collect the hydrogen bubbles into one part of the burette.

(3) mercury is toxic and very dangerous to human health.

(4) mercury prevents gas clinging to the inner wall of the glass tube from ascending.

(5) collector liquids in both methods are apt to include gas which clings to the sample surface.

(6) In addition to H$_2$ gas, small amounts of CH$_4$ and CO gas are also generated from the sample piece. Furthermore, N$_2$ gas and O$_2$ gas which have been clinging to the sample surface are included as well. Thus, reading the burette scale only makes it possible to determine the total amount of gas generated, but an accurate measure of diffusible hydrogen cannot be obtained.

(7) In the case of welding using a low hydrogen welding rod which is presently being developed, less than 1 ml diffusible hydrogen is included in 100 g weld metal. None of the above noted methods can achieve accuracy in this case.

In view of the above mentioned detects, the vacuum extraction method (gas burette extraction method) in which no collector liquid is used has been developed. However, in vacuum extraction leakage sometimes occurs, and air mixed with diffusible hydrogen may also be measured. Moreover, measurement error may occur due to temperature change, and this method is not satisfactory, either. Still further, even in this method, mercury has to be used for moving gas, which is not satisfactory from a safety stand point.

Recently, a technique for measurement of hydrogen with a gas chromatograph has been proposed in "Welding Research International Vol. 6 No. 3 pp 1–10". In accordance with this technique, a sample piece cooled according to the IIW method is inserted into an enclosed collector cylinder, and a portion of the diffusible gas within the collector cylinder is taken out and introduced into a gas chromatograph, then analyzed by recorder, thus a very small amount of hydrogen is measured with relatively high accuracy. However, in this method, a predetermined portion of sample gas has to be taken out by keeping the temperature and pressure of sample gas constant, because the volume of the gas is easily affected by gas temperature and pressure; but this is technically very difficult. And if it could be done, the analysis accuracy is still not satisfactory. Further, the apparatus is complicated and special skill and various corrections depending upon measurement conditions will also be necessary. Thus this method is not practical.

SUMMARY OF THE INVENTION

The present invention has been made in view of the above mentioned defects of the prior art, and the object of the present invention is to provide an improved process for accurate, simple and safe measurement of diffusible hydrogen within metal. Another object of the present invention is to provide an improved apparatus to carry out the above noted process.

In order to accomplish the above objects, there is provided according to one aspect of this invention a process for measurement of diffusible hydrogen within a metal, which comprises the steps of placing a metal sample piece within an enclosed collector vessel for a predetermined time and at a predetermined temperature for gas effusion, and feeding the total effused gas within the vessel to a gas chromatograph.

In accordance with the second aspect of this invention there is provided a process of the type recited, wherein the total effused gas within the vessel is fed to the gas chromatograph at a flow rate of 150–1000 Nml/min. under a gas pressure of 1.5–26 kg/cm$^2$.

In accordance with the third aspect of this invention, there is provided a process of the type recited, wherein the separation system of the gas chromatograph comprises a separation column having an inner diameter of 1.6–7 mm.

According to the fourth aspect of this invention, there is provided a process of the type recited, wherein the inner diameter of the tubing; in the gas chromatograph is 1.6–7 mm.

According to the fifth aspect of this invention, there is provided a process as recited, wherein less than 30% of filler within the separation column of the gas chromatograph is finer than 35 mesh.

According to the sixth aspect of this invention, there is provided a process of the type recited, wherein less than 5% of the filler within the separation column of the gas chromatograph is finer than 150 mesh. According to the seventh aspect of this invention, there is provided an apparatus for measurement of diffusible hydrogen, which comprises; means for supplying an inert gas, means for regulating the inert gas pressure, means for measurement of the amount of the inert gas flow, means for collecting effused hydrogen, and means for feeding the total effused gas within the vessel to a gas chromatograph and means for regulating the flow rate of gas flowing into the gas chromatograph, wherein said gas chromatograph includes at least one separation column and thermal conductivity detector (TCD).

BRIEF DESCRIPTION OF THE DRAWINGS

Various other objects, features and attendant advantages of the present invention will be more fully appreciated as the same becomes better understood from the following detailed description when considered in connection with the accompanying drawings in which like reference characters designate like or corresponding parts throughout the several views, and wherein.

DETAILED DESCRIPTION OF PREFERRED EMBODIMENTS

Figure 1:
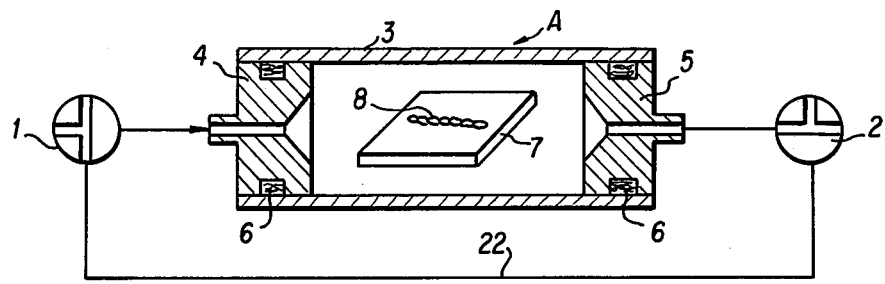
FIG. 1 is a schematic cross section of an enclosed collector vessel according to the invention.
Figure 2:
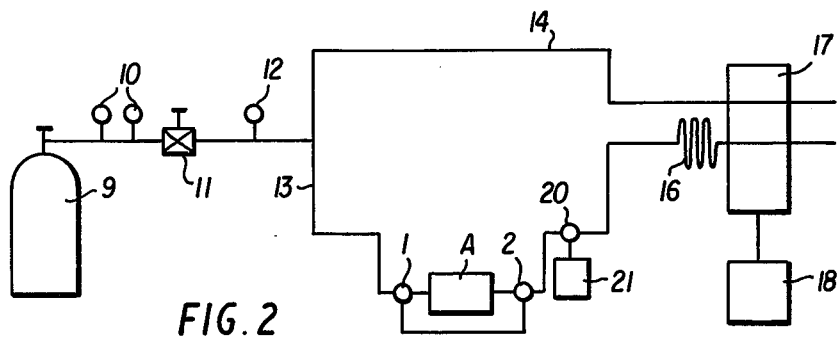
FIG. 2 is a schematic diagram of an apparatus according to the invention.

FIGS. 1 and 2 are explanatory views of an apparatus for carrying out the process of the invention. FIG. 1 shows a collector vessel cylinder A, and FIG. 2 shows an apparatus for measurement of diffusible hydrogen. The collector cylinder consists of cylindrical body 3 and plugs 4 and 5, within which a weld bead 8 on a test piece 7 is placed, thus this cylinder is kept sealed by means of O-rings 6. Plugs 4 and 5 are respectively connected to two-directional select cocks 1 and 2, between which a discharge passage 22 is provided.

Here, an explanation will be given for the case in which a hydrogen collector gas having smaller heat conductivity than that of hydrogen such as argon or nitrogen gas is used. Air can also be used as an $H_2$ collector gas. A steel plate on which a weld bead is formed is quenched in ice water according to the JIS method or the IIW method and thereafter cooled in dry ice/acetone or dry ice/methanol, and then placed within collector cylinder A as shown in FIG. 1. The above mentioned quenching in ice water suppresses the hydrogen diffusion coefficient by decreasing the temperature, and prevents hydrogen effusion from the earliest stage. And also cooling in dry ice to a temperature of approximately $-60°$ C. prevents hydrogen effusion from the sample piece before it is placed within the vessel cylinder. After the sample piece is placed within the cylinder, select cocks 1 and 2 are operated to a positions as shown in FIG. 1 and vacuum pump 21 is operated to remove air within the cylinder vessel to reduce the gas pressure to approximately $10^{-1}$ mmHg. The primary object of reducing the gas pressure is to improve analysis accuracy. If the temperature of a sample is near room temperature, effused gas would also be removed from the cylinder. Accordingly, cooling the sample to $-60°$ C. is quite meaningful in this respect.

If satisfactory reduction in gas pressure is not achieved during the pressure reduction step, it is possible that the sealing of the cylinder is not good enough, and diffusible hydrogen may get out of the system. In this sense, the pressure reduction operation is significant for checking the sealing effectiveness of the collector cylinder. The other object of the pressure reduction is to remove coolant such as acetone or alcohol, or dew drops clinging to the sample surface which has been cooled to $-60°$ C. If measurement of diffusible hydrogen is carried out without removing these clinging materials, $CO_2$ included in the coolants or moisture deteriorates the column packing, for example, molecular sieves, within the separation column.

Figure 3:
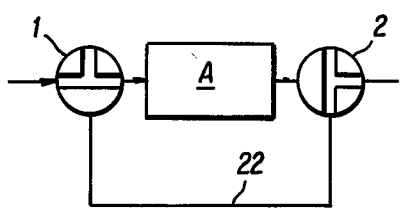
FIG. 3 is a schematic view showing operation of the select cocks.

When a vacuum condition is obtained, the sample piece may be left in the collector cylinder for a predetermined time to effuse hydrogen from the sample. On the other hand, a hydrogen collector gas such as Ar or $N_2$ which is identical to the carrier gas can be admitted to the cylinder vessel and diffusible hydrogen allowed to effuse for a predetermined time. When introducing Ar into the vessel, the Ar tank is opened after select cocks 1 and 2 are set to the position shown in FIG. 3. In FIG. 2, 10 represents a pressure reduction valve, 11 represents a pressure regulation valve, 12 represents a pressure guage, and circuits 13 and 14 and collector vessel A are filled with Ar. After the pressure within the vessel A is adjusted to atmospheric pressure, only cock 1 is turned to the position shown in FIG. 1. Then the collector vessel A which is filled with Ar is taken out of the apparatus and is put in a thermostatic oven kept at a temperature of 25°–45° C. as in the JIS method or IIW method, and is left therein for a predetermined time, for example, 48–72 hours, so that diffusible hydrogen may effuse from the sample.

If hydrogen collector gases different from the carrier gas are used, these gases have to be separated from hydrogen in a subsequent operation step, and separation column 16 must be extremely long or the flow rate of carrier gas has to be very small. This results elongation of the analysis time and is thus impractical.

Figure 4:
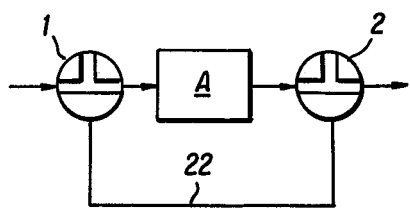
FIG. 4 is a schematic view showing operation of the select cocks.

When hydrogen effusion is finished, vessel A is again placed in the apparatus, select cocks 1 and 2 are operated to the position shown in FIG. 4 and simultaneously introduction of carrier gas(Ar) is started. As the result, Ar flows into circuits 13 and 14, and hydrogen and Ar within the vessel A are fed to the separation column 16.

Figure 5:
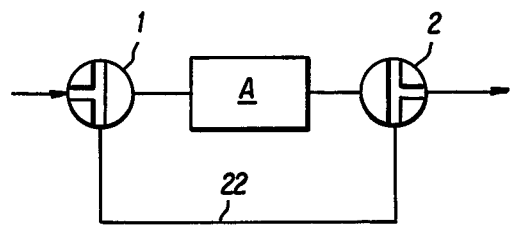
FIG. 5 is a schematic view showing operation of the select cocks.
Figure 6:
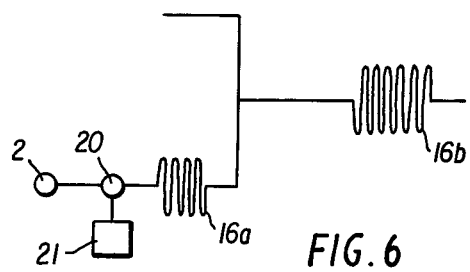
FIG. 6 is a schematic diagram showing an arrangement of separation columns according to the invention.

Separation of $H_2$ from the other mixture gases takes place in the separation column, and when the $H_2$ to be measured has passed through the select cock 2, select cocks 1 and 2 are operated to a position shown in FIG. 5. Accordingly, the separated $H_2$ gas is fed to TCD(Thermal Conductivity Detector) 17 by carrier gas that flows through the discharge passage 22, and is measured by an integrator 18 by comparison with the reference flow from the circuit 14. FIG. 2 shows only one separation column 16, but as shown in FIG. 6 precut column 16a and main column 16b may be used together at the front and rear portions of the separation system, respectively.

When measurement of diffusible hydrogen is finished, the vessel A is taken out of the apparatus, and the sample piece is removed from the vessel to be weighed. Since the present invention does not use glycerine or mercury, the sample piece does not have to be washed and there will be no fear of pollution of the collector liquid. If the weight of the sample piece is measured, it is compared with the original weight of the steel plate 7 and the net weight of the weld bead can be found, and this value is to be converted based on 100 g of deposited metal. Then diffusible hydrogen content per a certain weight of weld bead can be obtained in ml/100 g.

Figure 7:
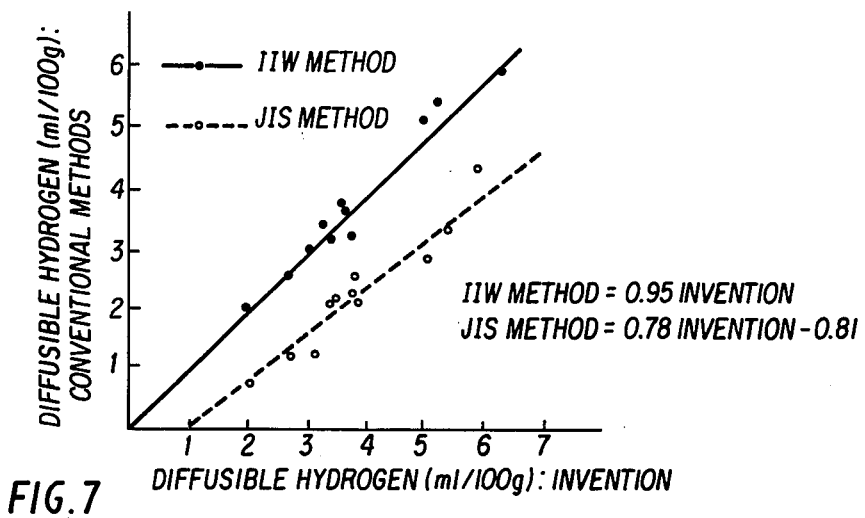
FIG. 7 is a graph showing comparison between the invention and prior art methods.

FIG. 7 shows results of comparative tests between the process of the invention and the prior art methods such as JIS and IIW methods, in which commercial low hydrogen welding electrodes are welded on the steel plates under various partial moisture pressures so that different amounts of diffusible hydrogen may be obtained from the thus obtained sample pieces in order to obtain comparative values in accordance with the invention, IIW and JIS methods, respectively.

Figure 8:
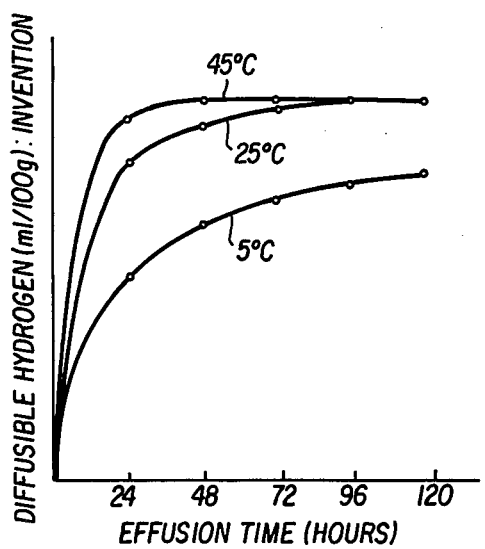
FIG. 8 is a graph showing a relationship between amount of diffusible hydrogen and diffusion time according to the invention.

As the results show, values obtained in accordance with the invention are slightly higher than those of the IIW method, and a considerably higher collection rate was obtained compared with the JIS method. The collection rate of IIW was 95% of that of the present invention, which reveals that the amount of hydrogen clinging to the sample piece and to the inner wall of the mercury bell in the form of small $H_2$ bubbles cannot be neglected. FIG. 8 shows the effect of temperature on $H_2$ effusion relative to diffusible hydrogen effusion rate. In the JIS or IIW method, the aggregation rate of the small $H_2$ bubbles which are generated affects the $H_2$ effusion curve. On the other hand, in accordance with the invention, such an effect does not take place, and an extremely smooth effusion curve is obtained.

Reviewing the relationship between effusion temperature and amount of hydrogen effusion, the effusion is complete in 48 hours at 45° C., and in 72 hours at 21° C. On the contrary, only 81% effusion can be obtained in more than 120 hours at a temperature of 5° C.

Now, the gas to be analyzed in the invention is hydrogen, so that air, i.e., atmosphere, can be used as hydrogen collector gas since the air includes no substantial hydrogen and its heat conductivity is less than 1/10 of that of hydrogen. The advantages of using the air as hydrogen collector gas are as follows;

(1) The air can also be used as carrier gas.

(2) Exhausting air from the vessel A is not necessary, and introduction of a special carrier gas such as Ar into the vessel after evacuation of the vessel is not necessary either. Accordingly, provision of vacuum pump (suction pump) 21, cocks 1a and 2a, and select cock 20 is not required and so the apparatus can be simplified.

(3) Because of advantage 2), further cooling of the sample piece in dry ice is not necessary after the welded sample is quenched in ice water and the quenched sample can immediately be inserted into the vessel A. Thus, preparation time can be shortened and operation can be simplified, so that $H_2$ effusion from the sample piece during the preparation step can be suppressed, resulting in improvement in analysis accuracy.

(4) With Ar gas as a carrier gas, circuit 14 is required for removing retained air at the rear portion of select cock 2 and at the forward portion of select cock 1 shown in FIG. 2, and Ar has to be always passed through these portions. However, when using air as carrier gas, the above consideration in not at all necessary. Accordingly, select cocks 1 and 2, and circuit 14 are not necessary, resulting in further simplifying the apparatus. Hence, moisture clinging to the sample surface right after quenching in ice water is introduced into the vessel A together with the sample itself, and no vacuum (suction) pump removes air within the vessel. In this case analysis accuracy is adversely affected by the moisture introduction. CO gas may be generated due to oxidation of the sample piece surface, which also adversely affects the accuracy. However, these problems can be solved by adopting an absorption tube filled with moisture removing agents and CO removing agents such as molecular sieves, silica gel, $P_2O_5$, $I_2O_5$, $Mg(ClO_3)_2$, NaOH and KOH. Instead of such an absorption tube, a precut column may be used by which moisture can be taken out of the system after hydrogen is taken out. In this case, the packing in the precut column may be "Porapak Q" (trade name of a product by Dow Chemical Inc.), "Carbosieves B" (trade name of a product by Spellco Inc.), and activated carbon which preferably do not absorb moisture.

The above described present invention permits performing an accurate measurement and simplifying the operation, in comparison with the JIS and IIW methods. According to a method disclosed in "Welding Research International Vol. 6, 1976, No. 3, once" effused $H_2$ is introduced into a detector tube, and measurement of $H_2$ has taken place, then the obtained value must be corrected relative to the volume ratio and the other factors. Accordingly, the volume ratios of the sealed vessel, detector tube and tube lines have to be extremely accurately known, and further the size of the sample piece, and error due to sealed vessel installation may also complicate the volume ratios. In contrast, none of the above mentioned defects can be found in the present invention since the total amount of effused hydrogen can be measured in this invention.

Of course, this invention should preferably be carried out with such a separation system as permits analyzing a large amount of gas so as to measure total hydrogen within the vessel. Unless such a separation system is used, it takes a long time for analysis. A preferable separation system to be used in carrying out the invention is hereinafter explained. A large amount of gas cannot be analyzed by the usual gas chromatograph, and usually one cannot be used when using a vessel having capacity over 10 ml. However the sample piece to be analyzed in this invention must be of considerable size, for example 12 mm thick, 25 mm wide, 130 mm long, as in the case of the JIS method. Thus, the cylindrical body A must be at least 30 mm in diameter x 130 mm in length, i.e., having a capacity of 91.8 ml. In this case, the gas flow rate from the vessel should be 50–100 N ml/min and the gas pressure should be 0.5–1.0 kg/cm$^2$. If used with the usual gas chromatograph, analysis takes an extremely long time.

Figure 9:
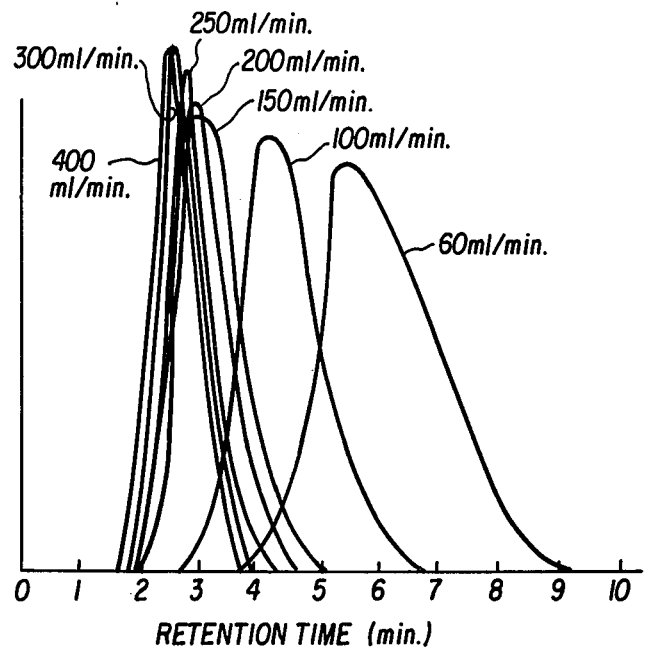
FIG. 9 shows extraction curves as observed when varying the flow rate of gas to be determined.

In view of these defects, the invention has been made after various trials of the inventors, and we found it necessary greatly to increase the amount of gas flow to be measured so as to feed gas with a large capacity vessel within a short time. FIG. 9 shows extraction curves as observed when changing the amount of gas to be measured for the case wherein the sample gas amount is 91.8 ml. As apparent from this FIG. 9, more, than 150 ml/min of gas flow is necessary to obtain a sharp peak with a short retention time. And even if the amount of gas flow is increased still more, the retention time cannot be drastically shortened, so that there is no upper limit to the amount of gas flow, but it can be said that 1000 Nml/min is enough in view of the ability of the apparatus. With respect to gas pressure for obtaining the above mentioned amount of gas flow, approximately 1.5–26 kg/cm$^2$ is preferable, and if over 26 kg/cm$^2$, leakage occurs at the joints of the separation system, which causes measurement error.

Now, having had considered the required conditions to obtain an amount of gas flow of more than 150 Nml/min, we found that both the inner diameter of separation column and the grain size of the packing within the column, significantly affect the above mentioned amount of gas flow.

Figure 10:
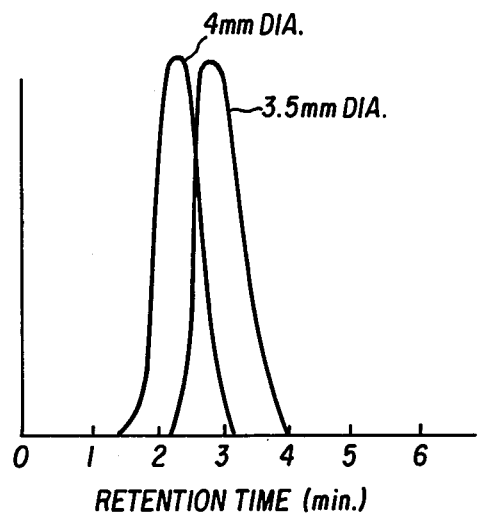
FIG. 10 is a graph showing the relationship between inner diameter of a separation column and retention time.

Making various columns having different inner diameters, we found that at least 1.6 mm is necessary to obtain an amount of gas flow of more than 150 ml/min. With an inner diameter of 1.6 mm, excess pressure does not have to be applied. With a column having inner diameter of less than 1.6 mm, an amount of gas flow up to 150 Nml/min could not be achieved even with excessive pressure being applied. As can be seen from FIG. 10 in which the amount of sample gas is 90 ml, as the inner diameter of the column becomes smaller, the retention time becomes longer. There is no upper limit in column inner diameter, however, when it is over 7 mm, the curve on the chart has a broad peak and analysis time becomes longer.

The inner diameter of gas line tubing within the system may be a little smaller than that of the column and should preferably be 1.6–7 mm for a practical use.

With respect to column packing, in accordance with the invention, since a large amount of gas flows through the column, the packing is crushed by a large gas impact pressure. Hence, if a large portion of the packing is fine grains, the desired amount of gas cannot flow through the column, and most of the fine grains are blown toward the rear end of the column resulting in shortening the effective length of column. And if air is used as carrier gas, since there is no cock within the system, switching shock causes an inaccurate analysis value. Accordingly, fine grains should desirably occupy a small proportion of the total packing.

In accordance with the invention, a small amount of slag and rust cling to the sample surface after the sample is quenched in ice water right after completion of welding. So that dust generated from such slag or rust is also introduced into the separation system together with carrier gas, and may enter into the separation column. Dust and fine grains which are a little coarser than the dust may prevent gas from flowing through the column.

Figure 11:
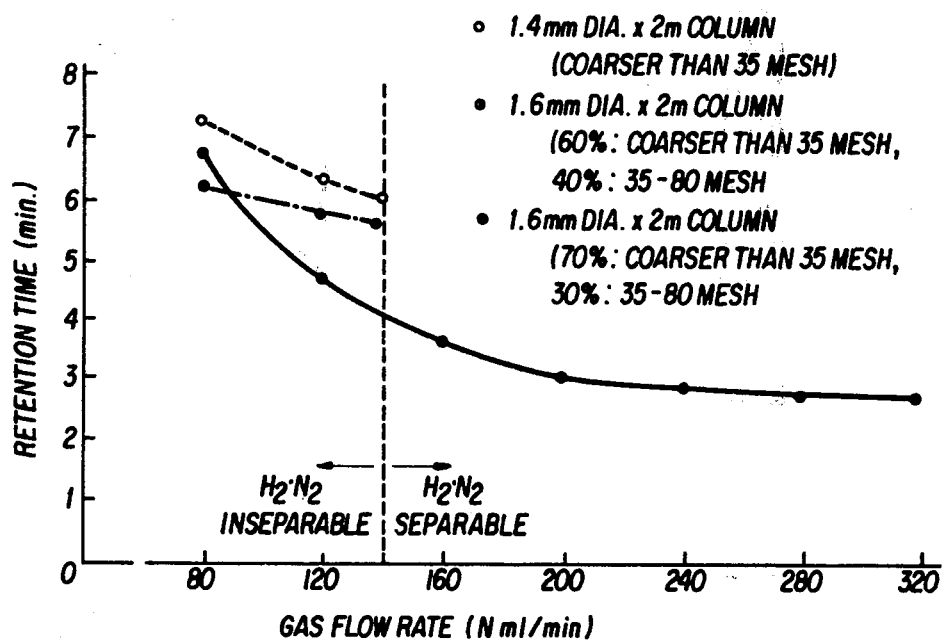
FIG. 11 is a graph showing the relationship between gas flow rate and retention time as observed when varying the inner diameter of the separation column and the grain size of the filler within the column.

FIG. 11 shows the relationship between the amount of gas flow to be measured and retention time, when varying the inner diameter of the column and grain size of the packing when the amount of sample gas is 90 ml. Even when the inner diameter of the column is 1.6 mm, if the grain size of the filling agents is 35–80 mesh, a gas flow over 150 ml/min could not be obtained, i.e., separation of $H_2$ from $N_2$ is impossible. While if more than 70% of the packing is coarser than 35 mesh, sufficient gas flow could be obtained with shorter retention time, i.e., separation of $H_2$ from $N_2$ is possible. When the column inner diameter is 1.4 mm, the upper limit of the amount of gas flow was 150 ml/min even with packing coarser than 35 mesh.

Having repeated these experiments, it was found that the object of the present invention is satisfactorily achieved if the packing is so adjusted that less than 30% is finer than 35 mesh, and less than 5% is finer than 150 mesh. Any materials hereinbefore mentioned can be used as packing according to need, but for example when measuring $H_2$ amount within slag, flux or diffusible $H_2$ within steels, molecular sieves are used in practice for their good separation of $H_2$, $N_2$ and $O_2$.

However, molecular sieves are easily crushed. In this respect, restriction of grain size of the filler is especially important. Since the invention is consisted as above described, diffusible hydrogen within weld metal of steel material can be accurately, simply and promptly determined. And measurement of total effused hydrogen makes it unnecessary to correct obtained values, and further permits measuring $H_2$ even from a very small sample piece.

Accordingly, the present invention contributes to extremely improve analysis accuracy. Obviously, numerous modifications and variations of the present invention are possible in light of the above teachings. It is therefore to be understood that within the scope of the appended claims, the invention may be practiced otherwise than as specifically described herein.

What is claimed as new and intended to be covered by Letters Patent is:

1. A process for measurement of diffusible hydrogen within a solid metal, which comprises the steps of:
    placing a metal sample piece within an enclosed gas collecting means for a predetermined time at a predetermined temperature so that diffusible hydrogen may be effused from said metal sample piece while in the solid state; and then
    feeding the total effused gas within said gas collecting means to a gas chromatograph equipped with a separation column having an inner diameter of 1.6–7 mm containing packing wherein less than 30% of said packing is finer than 35 mesh and less than 5% of said packing is finer than 150 mesh, and measuring said diffusible hydrogen.

2. The process set forth in claim 1, wherein said total effused gas within said gas collecting means is fed to said gas chromatograph at a gas flow rate of 150–1000 Nml/min under a gas pressure of 1.5–26 kg/cm$^2$.

3. The process set forth in claim 1, wherein the inner diameter of gas line tubing within said gas chromatograph is 1.6–7 mm.

4. An apparatus for measurement of diffusible hydrogen with a solid metal sample, which consists essentially of:

a gas collecting means for collecting diffusible hydrogen from said metal, and in fluid communication with said gas collecting means, a gas chromatograph which includes a separation column having an inner diameter of 1.6–7 mm and a packing wherein less than 30% of the packing is finer than 35 mesh and less than 5% of the packing is finer than 150 mesh, a thermal conductivity detector, and an integrator for measuring the volume of said diffusible hydrogen, and a gas supply means for supplying an inert carrier gas to said gas collecting means and gas chromatograph whereby said diffusible hydrogen is transferred from said gas collecting means to said gas chromatograph, said gas supply means including a source of insert carrier gas, means for regulating the pressure of said inert carrier gas, and means for measuring the flow rate of said inert carrier gas; and means for regulating the flow rate of said carrier gas to said gas chromatograph.

* * * * *